United States Patent [19]

Sproviero et al.

[11] Patent Number: 5,374,274
[45] Date of Patent: Dec. 20, 1994

[54] METHOD FOR FACILITATING SAFE REMOVAL OF TICKS FROM HOST VICTIM USING ELECTRICAL PULSES

[76] Inventors: Joseph Sproviero, 70 Kellers Farm Rd., Easton, Conn. 06612; Frank Ellul, 10 Preston Pl., Patterson, N.Y. 12563

[21] Appl. No.: 126,606

[22] Filed: Sep. 27, 1993

[51] Int. Cl.$^5$ .................... A61B 17/36; A61B 17/28
[52] U.S. Cl. ..................... 606/131; 606/32; 128/898
[58] Field of Search .............. 606/1, 32, 34, 41, 49, 606/52, 131, 205–211; 452/58, 57; 128/898

[56] References Cited

U.S. PATENT DOCUMENTS

| | | | |
|---|---|---|---|
| 2,888,927 | 6/1959 | Fozard | 606/36 |
| 3,012,271 | 12/1961 | Morse | 452/58 |
| 4,213,460 | 7/1980 | Weiner | |
| 4,303,268 | 12/1981 | Davidson | 294/16 |
| 4,442,837 | 4/1984 | Keatley | |
| 4,461,297 | 7/1984 | Sutter | 606/210 |
| 4,566,454 | 1/1986 | Mehl et al. | 606/36 |
| 4,976,718 | 12/1990 | Daniell | 606/131 |
| 4,979,771 | 12/1990 | Childs, III | 294/99.2 |
| 5,002,323 | 3/1991 | Idsund | 294/100 |
| 5,026,369 | 6/1991 | Cole | 606/36 |
| 5,078,729 | 1/1992 | Eichhorn | 606/210 |
| 5,116,347 | 5/1992 | Butler | 606/131 |

*Primary Examiner*—Stephen C. Pellegrino
*Assistant Examiner*—Glenn K. Dawson
*Attorney, Agent, or Firm*—H. Gibner Lehmann; K. Gibner Lehmann

[57] ABSTRACT

A tick extracter consisting of a pair of manually operable, electrically insulated jaws in the form of tweezers adapted to grasp the body of the tick, and an electrical source to supply one or more electrical pulses to the jaws so as to jolt the tick and cause it to loosen its grip on the flesh of the victim. The electrical source can be a piezo-electric crystal connected to the jaws of the tweezers by a flexible electrical cord, and can be manually controlled as by another hand, to effect the production of the electrical pulses from the crystal.

12 Claims, 1 Drawing Sheet

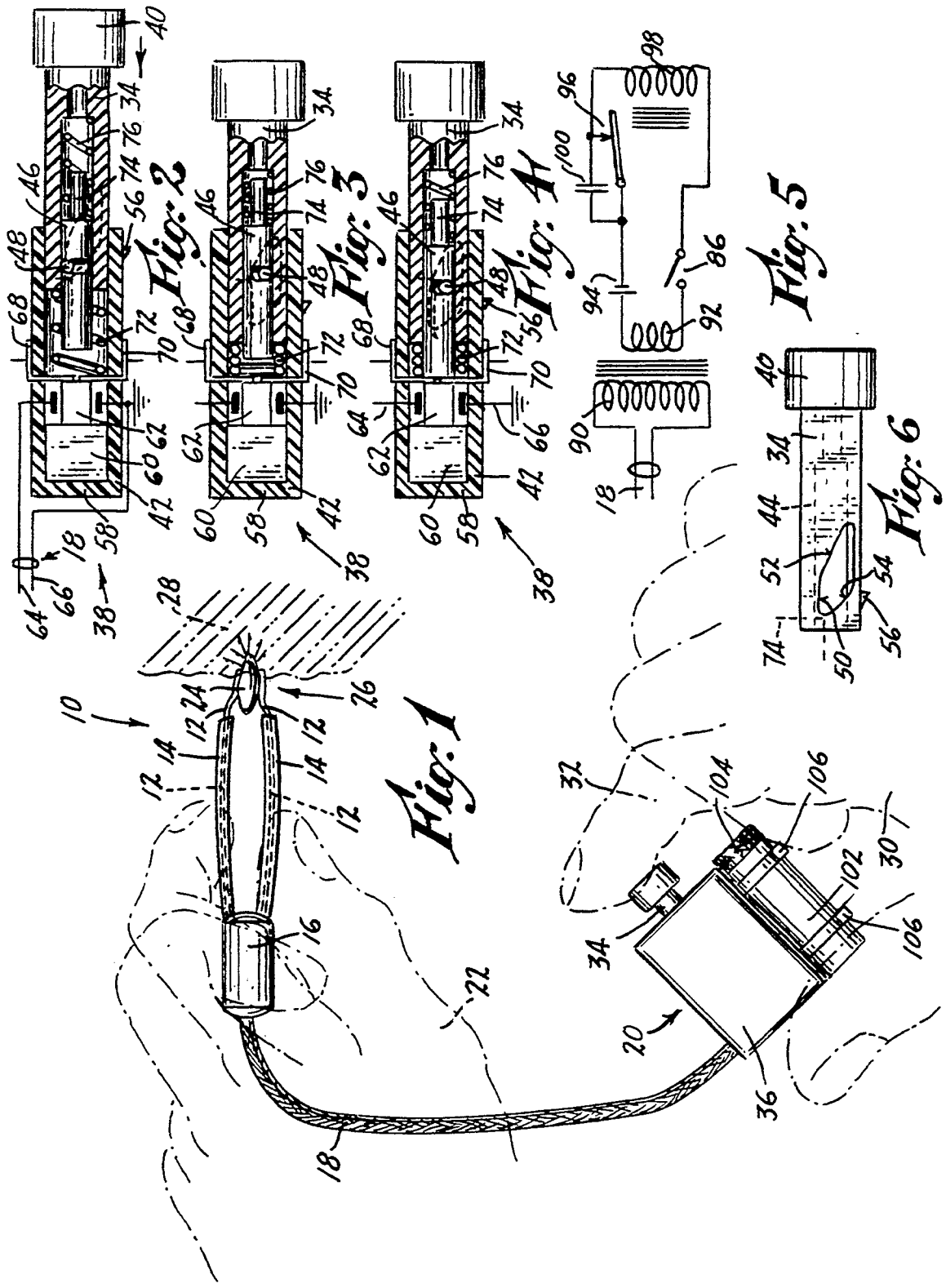

METHOD FOR FACILITATING SAFE REMOVAL OF TICKS FROM HOST VICTIM USING ELECTRICAL PULSES

NO CROSS REFERENCES TO RELATED APPLICATIONS

STATEMENT AS TO RIGHTS TO INVENTIONS MADE UNDER FEDERALLY-SPONSORED RESEARCH AND DEVELOPMENT

Research and development of the present invention and application have not been Federally-sponsored, and no rights are given under any Federal program.

BACKGROUND OF THE INVENTION

1. Field of the Invention

This invention relates to apparati and methods for removing ticks, and more particularly to improvements over known methods and instruments of the kind normally employed in removal of such insects. 2. Description of the Related Art Including Information DISCLOSED UNDER 37 CFR §§1.97–1.99

Disease, as transmitted by ticks, has been widely documented over the years.

A brief listing is contained in U.S. Pat. No. 5,116,347, issued May 26, 1992. Specifically, col. 1, lines 19–24 specify, ". . . Lyme disease, Rocky Mountain spotted fever, Colorado tick fever, tularemia, relapsing fever, tick paralysis, and ricksettial diseases; and Lyme disease, anaplasmosis, babesiosis, equine and St. Louis encephalitis, Q fever, spirochetosis, and toxoplasmosis in animals."

In the 1800s, early settlers in this country became afflicted with what has come to be known as Rocky Mountain Spotted Fever, referred to above.

More recently, Lyme disease has gained national attention, particularly in the Northeastern United States.

The booklet HEALTH AND DISEASE, published by Life Science Library, Time Life Books, Time Incorporated, 1965, authored by Rene Dubos, Maya Pines, and the Editors of Life Magazine, provides a brief description of Rocky Mountain Spotted Fever. The disease was initially thought to be carried by a type of tick known as the Rocky Mountain Wood Tick. Subsequently, it has been determined that this tick has infected a number of other varieties of ticks. Rocky Mountain Spotted Fever is characterized by a rash, high fever, and aching joints. Untreated, the disease can lead to death. Initially discovered in the area for which it was named, the disease is now known to have spread to vast areas of the Western Hemisphere.

The "disease" is actually the effect of a spirochete microorganism, which is a bacterium larger than a virus. The microorganisms live and multiply within ticks. The ticks, in turn, infest a series of animal hosts. As larvae and nymphs, ticks feed on the blood of rabbits, rodents, and the like. As adults, they attach themselves to larger mammals, including man. Though certain animals infested with ticks are sometimes not harmed by the micro-organism, in the human body there occurs damage to the walls of small blood vessels. In advanced stages, the malady results in widespread lesions and moderate to severe internal hemorrhaging throughout the human body.

Kyasanur Forest Disease is another tick-transmitted ailment. This virus was discovered in 1957, having as its most prominent symptom, a very high fever. Infected ticks carried by certain birds transmit the virus. The virus was initially isolated in India, but is believed to have spread due to migration of the birds.

While avoidance of the offending tick is probably considered the best defense against the diseases noted, obviously this is not possible.

As a consequence, a number of methods and instruments for removal of ticks have been proposed over the years, as illustrated by the following sample of patents, which are cited as being of general interest in the field to which the invention pertains:

U.S. Pat. Nos.: 4,213,460 4,303,268 4,442,837 4,976,718 4,979,771 5,002,323 5,078,729 5,116,347

A widely prevalent procedure has been to physically grasp the tick with a tweezers and attempt to pull it directly out of the skin of the host.

This method, while extensively employed, is seriously deficient for a number of reasons. More often than not, the personnel manipulating the tweezers is often not particularly skilled in the field. What typically occurs is that the tick's body is either broken off, leaving the mouth or proboscis of the tick embedded in the skin, or else, the tick's body is squeezed to the extent that some of the fluid from the tick is actually spewed into the host's wound.

Along with the present widespread concern over Lyme disease, infected ticks have become a serious problem in many parts of the country. Lyme disease, while treatable in its early stages, is considered a serious malady if left untreated. It is capable of causing permanent damage to the body's organs and nerves, and in extreme cases, death. Paralysis and/or severe physical disabilities often ensue in cases where the disease is not diagnosed sufficiently early, and where appropriate medical treatment is not instituted promptly upon confirmation of the presence of the disease.

A typical example of an apparatus and method that have been devised for the purpose of removing ticks is disclosed in U.S. Pat. No. 4,213,460. The patent illustrates a method involving the applying of a forceps to a tick simultaneously with the application of either heat or else a chemical irritant, so as to disturb the tick and purportedly "relax" the tick's body. The inventor claims that he has found suitable chemical relaxants to include alcohol, gasoline, and kerosine, col. 4, lines 30–32.

However, other people have found that the use of heat and/or chemicals can actually impede a safe removal, since the tick may well be killed outright, as opposed to merely disabled, and it is apparently not well documented medically, at least in this patent, that the use of such heat and/or chemical irritant actually attains the desired result, namely causing the tick to release its hold in the host's tissue.

A somewhat similar approach is illustrated and described in U.S. Pat. No. 4,979,771, which discloses tweezers having heater elements at the ends of the tweezers, which elements contact the tick's body during the removal procedure. The heat allegedly relaxes the tick's body to facilitate the removal, as explained in col. 1, lines 24–28 of the patent. Although the patent contains a statement to the effect that the tick's head will not be crushed during the removal procedure, col. 2, lines 5–9, the implementation of this objective is not explained in any detail, since there is disclosed only one size of tweezers, whereas ticks vary considerably in size, depending on the type of tick. In particular, they can be just barely visible to the eye, i.e. comparable in diameter to that of a typographical period at the end of a sentence in a typical newspaper column; or alternately they can be considerably larger, as for example, comparable to the size of a small pea.

Other patents noted above disclose passive instruments for removing ticks/parasites.

In particular, U.S. Pat. Nos. 4,303,258 and 4,442,837 disclose instruments incorporating sliding sleeves on tweezers, which allegedly facilitate grasping the tick and holding it while manipulating the instrument. The same is true of U.S. Pat. No. 5,002,323.

U.S. Pat. Nos. 4,976,718; 5,078,729; and 5,116,347 illustrate different constructions of passive instruments adapted for use in removing parasites.

That there still exists doubt as to a universally approved technique for removing ticks, reference is made to col. 1 of U.S. Pat. No. 5,116,347, lines 40–48, wherein the inventor has cast some doubt on the efficacy of the present methods employed in tick removal; in particular the patent specifies, ". . . This new medical knowledge also indicates that the most common methods of removing ticks—such as with the fingers, with tweezers, by applying heat, dousing the parasite with a chemical, or rotating the parasite about its longitudinal axis in efforts to dislodge its imbedded proboscis—are undesirable, and in some cases can actually promote the spread of this and other tick-borne diseases."

Further, note is made in col. 2 of this patent, first and second full paragraphs, of the remarks in reference to an undesirable activation of the tick's autonomic reflex process of regurgitation in response to heat or chemical stimuli.

Finally, the tick, once removed, is usually sent to a laboratory for analysis in order to determine the presence of the Lyme disease bacteria (or disease-producing microorganism, as the case may be). This is best accomplished if the tick is still alive, following its removal. Where the tick has been killed, or badly mutilated by the tweezers, the analysis by public health personnel is made more difficult and with less certainty, which is a distinct disadvantage because the host victim is then faced with the possibility of latent infection and difficulty in having a physician diagnose the presence of disease, due to the questionable nature of the blood tests currently employed, and variations in the incubation period of the disease. In many instances of Lyme disease, symptoms do not become apparent until many weeks after the tick "bite" has occurred.

Where the tick has been successfully removed, storage of the live parasite, for transmittal to the laboratory, is awkward. There is the distinct possibility of inadvertent release of the tick from the tweezers immediately after removal. Were the tick to drop onto the floor, or worse, at a road side or in a wooded area, the problem of locating the body and recovering it can be readily appreciated.

Thus, there has existed a long-felt need for a safe method of removing ticks, especially without undue risk of breaking off the tick's body parts and leaving them embedded deeply in the host's skin; there is also the need to avoid any procedure which might cause the tick to propel fluid into the host's wound at the site of attachment.

Additionally, there has been a need to provide a means for convenient storage of the tick's remains in a safe and efficient manner, preferably to preserve the capability for subsequently examining the tick's body for presence of the Lyme spirochete, at a suitable public health facility or laboratory.

The problem of safely removing a tick has been addressed in the prior art of which we are aware, but a satisfactory solution to the problem appears to be lacking, as of the present time.

SUMMARY OF THE INVENTION

The problems noted above in connection with safe removal and disposal of a tick from a host victim are largely obviated by the present invention, which has for one object the provision of a novel and improved apparatus for easily, quickly and safely removing ticks, which apparatus is both simple in its structure and easy to use, even by relatively unskilled personnel.

Yet another object of the invention is to provide an improved apparatus as above set forth, which effectively forces the tick to release its hold in the tissue of the host, essentially completely without the use of excessive force or twisting, and without the need for flame-generated heat, chemicals and the like.

Still another object of the invention is to provide an improved apparatus of the kind indicated, wherein the procedure of removing a tick can be accomplished in an absolute minimum of time, and with little physical effort and skill being required by the operating personnel.

A further object of the invention is to provide an improved apparatus as above characterized, wherein there is largely eliminated the possibility of tearing or breaking of the tick's body and the resultant expulsion of the tick's body fluids into the wound of the host.

Still another object of the invention is to provide an improved apparatus as above described, which largely eliminates any tendency for the tick to regurgitate into the skin of the host as a consequence of the stimuli of the removal procedure. Thus, the possibility of infection of the host is lessened.

Still another object of the invention is to provide an improved apparatus as outlined above, wherein a convenient storage facility for the tick's remains is provided, preferably incorporated in the apparatus, either integrally, or as a removable storage receptacle.

Yet another object of the invention is to provide a novel and improved method for removing ticks from a host, which method is considered safer than prior known methods, in that the possibility of contamination of the host at the site of the tick is considerably reduced through the elimination of the need to tear or otherwise mutilate the tick's body during its removal.

In addition, the novel method effectively minimizes the possibility of inadvertent regurgitation by the tick as a consequence of external stimuli during the removal procedure thus further avoiding the likelihood of infection of the host.

Still another object of the invention is to provide a novel and improved method as outlined above, which can be readily carried out essentially with one simple apparatus, preferably with the use of both hands, and wherein an especially precise positioning of the parts of the apparatus is made possible, thereby avoiding problems noted above in connection with mutilation and/or tearing of the tick's body. There is effectively eliminated any need for multiple instrument components, chemicals, and matches/cigarette lighters or the like, for generating heat.

A further object of the invention is to provide a novel and improved method as above characterized, wherein a disabling stimulus is applied to the tick and wherein the degree of the disablement is easily controllable manually; stated differently, an initial stimulus can be applied to the tick and a determination thereafter made as to whether the tick has responded. If not, additional stimuli can be applied in rapid succession and to any extent necessary in order to achieve the desired degree of disability to the tick, as visually observed by the user of the apparatus.

In accomplishing the above objects the invention provides a tick extracter comprising, in combination a pair of hand-held manually-operable jaws at least one of which is electrically conducting, electrical insulation means for insulating the one jaw from the hands of a user, the jaws being adapted to engage and grip opposite sides of the body of a tick that is attacking the flesh of a victim. The jaws enable a user to apply a gentle extracting force to the tick. There are further provided electrical pulse generating means connected with the one jaw for applying a shocking electrical pulse thereto, said pulse-generating means being capable of providing a shocking electrical bolt to the one jaw so as to jolt the tick into loosening is grip on the flesh of a victim.

The objects are further accomplished by a tick extracter comprising, in combination a pair of hand-held electrically-conducting manually-operable jaws both of which are electrically insulated from each other and which are adapted to engage and grip opposite sides of the body of a tick that is attacking the flesh of a victim. The jaws enable a user to apply an extracting force to the tick. In addition, electrical pulse-generating means are connected with the jaws for applying a shocking electrical pulse thereto. The pulse-generating means is capable of providing a shocking electrical energization to the jaws to jolt a tick into loosening its grip on the flesh of a victim.

The invention is also accomplished by a method of extracting a tick from the flesh of a victim, which includes the steps of applying a pair of jaws to the body of the tick and thereafter applying an electrical pulse to the tick's body to jolt the tick into releasing its grip on the flesh of the victim.

The invention is further accomplished by a method of two-handed extraction of a tick from the flesh of a victim, which includes the steps of applying a gripping instrument to the body of the tick with one hand, and actuating an electrical pulse generator with the other hand while simultaneously applying the pulse to the gripping instrument to be impressed on the tick's body so as to jolt the tick into loosening its grip on the flesh of the victim. The arrangement is such that the gripping instrument can take the form of a simple tweezers-like device, and can be held in one hand with great precision, due to its light weight and physically small size. Manipulation of the tweezers during both the phase involving application of the electric shock to the tick, and during the subsequent phase involving physically pulling the tranquilized tick with the same tweezers through which the shock was transmitted, is readily accomplished, without undesired break-up of the tick's body and without likelihood of regurgitation by the tick into the skin of the host.

The use of chemical agents is not required. Nor is use of heat, be it electrically-generated or flame-produced.

Other features and advantages will hereinafter appear.

BRIEF DESCRIPTION OF THE DRAWINGS

FIG. 1 is a plan view of the improved tick removing device of the invention, showing the tweezer portion of the device grasping a tick embedded in the flesh of a victim, and showing in broken outline the hands of a user holding the tweezers and holding a coupled voltage producing instrument or generator for applying a high, relatively "cold" as opposed to plasma, e. m. f. to the tweezer prongs.

FIG. 2 is an axial sectional view of a piezo-electric voltage producing instrument or generator such as shown in FIG. 1, in its cocked position.

FIG. 3 is a view like that of FIG. 2, but showing an intermediate position of the parts of the voltage producing instrument.

FIG. 4 is a view like that of FIGS. 2 and 3 but showing the voltage discharging position of the parts of the voltage producing instrument, FIG. 5 is a schematic circuit diagram of an alternate form of electric pulse producing instrument, and FIG. 6 is a plan view of the plunger part of the generator instrument of FIGS. 2–4.

DESCRIPTION OF THE PREFERRED EMBODIMENTS

Referring first to FIG. 1, the improved tick removing device of this invention comprises a tweezers 10 having a pair of resilient metal prongs 12 which are in part diagrammatically represented by dotted lines, said prongs being electrically insulated from the touch with an insulating plastic or rubber coating 14 as by virtue of having been suitably masked and dipped in a bath of such material.

As provided by the invention, the prongs 12 are imbedded in an insulating plastic connector and yoke block 16 in which are also embedded lead wires (not shown) of a coaxial connector cable 18, said wires being respectively connected to the prongs 12 to provide energy thereto.

Also, in accordance with the invention the coaxial cable 18 is connected to the output of a known type of piezo-electric pulse generator 20 the details of which are given in FIGS. 2–4.

Although the connecting cable 18 is designated as coaxial, any insulated flexible two-wire cable or lead wire means can be substituted therefor, as will be understood, it being merely necessary for the cable to have the ability to conduct pulses or energy to the tweezer prongs 12 from the generator 20.

Piezo-electric generators such as the generator 20 have been produced and sold in large quantities in the past, in connection with cigarette lighters, and are well known as to their construction; the generator 20 is described in some detail below to facilitate a complete understanding of the present invention, although per se the general construction and operation of the generator, together with its principles, are already known in the prior art.

The tweezers 10 are shown as being held by the left hand 22 of a user, and as gripping the body 24 of a tick 26 which has become partially embedded in the flesh 28 of a victim, whereas the piezo-electric pulse generator 20 is shown as being held by the right hand 30 of the user, with the forefinger 32 applied to the plunger 34 of the generator 20 in readiness to actuate the same to produce thereby electrical pulses of high voltage or magnitude, as for example even sufficient to jump an air gap of approximately ⅛".

We have found that, by the application of such pulses from a piezo-electric generator, the tick 26 is jolted considerably and sufficiently to cause it to release its grip on the flesh 28 of the victim suffering the tick bite. The plunger 34 can be repeatedly quickly actuated by the user while the generator is held in the fashion indicated in FIG. 1 without disturbing the force exerted by the user on the tweezers or disturbing the grip on the tick 26 by the tweezers 10, this being made possible by the use of the flexible connecting cable 18 between the tweezers 10 and generator 20, and this is an important feature of the invention.

The piezo-electric generator 20 has a rectangular casing 36 in which there is mounted a spring-charged manually-operated hammer mechanism designated generally by the numeral 38 in FIGS. 2–4. This hammer mechanism comprises the plunger 34 mentioned above, having a manually engageable button 40 which is external to the casing 36, and a deep cup-shaped housing 42 in which the plunger 34 is slidably received. The housing 42 has a square bore, and the plunger 34 has a complementary square exterior configuration for a sliding fit in the housing.

Referring to FIG. 6, the plunger 34 has a round bore 44 in which there is slidable a "hammer" bolt 46 provided with a transverse follower pin 48 that is captive in a cam slot 50 in one wall of the plunger 34. The cam slot 50 has camming edges 52 and 54 that act on the pin 48.

Retention of the plunger 34 in the housing 42 is effected by a stop finger 56 which is slidable in a slot (not shown) in one wall of the housing 42.

Lodged against the end wall 58 of the housing 42 is a cube-shaped mass 60 which can be of steel, and which functions as an anvil to back up a piezo-electric crystal 62 which has electric leads 64 and 66 passing through the housing 42. The mounting of the crystal 62 places it in the path of movement of the hammer bolt 46 so that movement of the bolt to the left as seen in FIGS. 2, 3 and 4 will enable it to exert a striking force against the crystal 62.

For purposes later described, two switch contact plates 68, 70 are carried by the housing 42 and disposed in the path of the hammer bolt 46. These contact plates transmit blows from the hammer bolt 46 directly to the piezo crystal 62. They also are electrically connected with each other or bridged when contacted by the hammer bolt, so as to function as a switch (later referred to).

The plunger 34 is normally biased to the right by a helical compression spring 72, and in so doing the spring causes the plunger 34, via the camming edge 54, to bias the hammer bolt 46 to the right, with the pin 48 biased upward for engagement with a stop 74 indicated by dotted outline in the figurers, which is on the inside of the proximal wall of the boy, sing 42 as viewed in the figures.

The hammer bolt 46 has an axially extending pin 74 encircled by a helical compression spring 76 located in the bore 44 of the plunger 34, thereby to bias the hammer bolt 46 to the left as viewed in the figures. This charges the bolt for its function to strike the crystal 62. The charged condition of the spring 76 is shown in FIG. 3, and the discharging position in FIG. 4. The spring 76 bears against a shoulder of the hammer bolt, as shown, to exert its influence. The piezo crystal 62 has its output leads 64, 66 connected to the cable 18 as indicated in FIG. 2.

Operation of the piezo generator unit is briefly as follows: Starting with the "at rest" position of FIG. 2 the operator depresses the button 40 so as to drive the plunger 34 to the left as viewed in this figure. Initially this takes up a slight bit of slack or lost motion which is built into the hammer mechanism 38, after which further leftwise movement of the plunger 34 as seen in FIG. 3 causes the camming edge 52 of the cam slot 50 to shift the follower pin 48 downward as shown, out of contact with the housing stop 74 that is indicated by the dotted lines in FIG. 6. During this movement, the compression return spring 72 is being compressed, taking the loading off of the hammer bolt 46. The hammer drive spring 76, after downward movement of the follower pin, now drives the hammer bolt 46 strongly toward the left, causing it to forcibly strike the switch plates 68 and 70 with considerable force which is transmitted to the piezo crystal 62 that is backed up by the anvil 60. The result is a brief but forceful mechanical stress applied to the crystal 62, resulting in the latter producing an extremely short "cold" (as opposed to a plasma) voltage burst or pulse of high magnitude at the piezo leads 64, 66 which is in the nature of a voltage spike of surprisingly sufficient magnitude to jump a spark gap of roughly ⅛". This energy in the tweezer prongs 12 will jolt the tick 26, causing it to lose its grip on the victim's flesh 28 and enabling the operator to easily pull the tick out therefrom. The actuation of the piezo generator can be repeated any number of times, all without disrupting the grip of the tweezers 10 on the tick's body or in any way changing the forces exerted thereon unless the operator so desires.

The operator's left hand which holds the tweezers 10 can be rested on any convenient surface during this procedure, as can be understood, without interference due to the operation of the piezo generator 20.

As presently understood, the jolting effect on the tick 26 does not depend on the ability of the generator to produce a jump spark. It is considered that voltages lower than sparking voltages and having an undulating characteristic may be sufficient to make the tick release its grip. Essentially the desired effect is obtained as a result of applying sufficiently high voltages to the body of the tick, as by the use of the insulated tweezer tongs, until the tick loosens its grip. A great advantage in the use of a piezo-electric generator of the kind illustrated, is that no batteries of any type need be used or relied on, since the generator is always reliable and ready to produce the desired electrical energy.

Another, alternative type of voltage generator which can be advantageously utilized with the tweezers 10 and cable 18 is illustrated in FIG. 5. The high-voltage producer in this figure can be activated by a switching device which has been built into the hammer mechanism of FIGS. 2–4; however, other types of switches could be used instead.

In FIG. 5 the function of the manually-operable switch 86 can be assumed by the switch plates 68, 70 shown in FIGS. 2–4 since these plates are only bridged by the hammer bolt 46 when the latter is in the force-delivering position of FIG. 4.

FIG. 5 shows a miniature voltage step-up transroomer whose secondary 90 can be connected to the cable 18 to deliver voltage to the tweezers 10 in place of a piezo-electric pulse. The transformer primary 92 is connected through a battery 94 and relay contacts 96 to a relay coil 98 which connects to the manually operable switch 86 and back to the primary 92. A capacitor 100 bridges the contacts 96. Closing of the switch 86 causes the relay coil 98 to be continually energized and de-energized, resulting in vibration of the relay armature and creation of a high pulsating voltage in the secondary coil 90. This will cause the energy thereof as delivered to the tick 26 to cause the latter to loosen its grip and enable the operator to easily remove the insect.

Further in accordance with the invention there is provided on the casing 36, a container 102 having a closure cap 104, the container 102 being removably carried by means of resilient retainer clips 106. Following removal of the tick by the method of the invention, the body (or residual parts thereof) can be placed in the container 102 and the cap 104 applied. The container housing the live tick can thereafter be shipped to a health facility or laboratory, for analysis, and subsequently disposed of by the laboratory personnel.

In use, a supply of containers 102 would be kept on hand, and used as needed following successful removal of a ticks, as embraced by the method of the present invention.

It is noted that examination of the suspect tick is facilitated if the insect can be removed without killing it. Under such circumstances, the live tick can be immediately transferred from the tweezers to the container 102, thereby avoiding the possibility of inadvertently dropping the tick, and having to search for it on a floor, or worse yet, amongst grass or in wooded areas.

The novel method of the invention is thus seen to embrace a process for extracting a tick from the flesh 28 of a host victim, which includes the steps of applying a pair of jaws such as 14, to the body 24 of the tick 26 and thereafter applying one or several electrical pulses to the tick's body 24 to jolt the tick into releasing its grip on the flesh 28 of the victim. As presently understood, the pulses can be of a waveshape characterized by consecutive peaks all of the same polarity, as would be produced by the piezo-electric generator 20. In a preferred embodiment, the jaws are applied to the tick 26 with one hand such as the left hand 22, and the electrical pulses are produced using the other hand, for example the right hand 30.

This method of two-handed extraction of a tick from the flesh of a victim, which includes the steps of applying the gripping instrument 10 to the body of the tick with one hand, and actuating an electrical pulse generator 20 with the other hand to simultaneously apply pulses to the gripping instrument 10 to be impressed on the tick's body so as to jolt the tick into loosening its grip on the flesh of the victim, is thus considered to be an important feature of the present invention. In carrying out the method, the flexible lead wire or cable 18 permits limited relative movement of the casing 36 as the plunger 34 is depressed, as occurs inadvertently because of the substantial force required to depress the plunger 34, all without disturbing the positioning of the tweezer prongs 12 on the tick's body. Thus, there is physical isolation between the casing 36 and the tweezers 10, and the precision and steadiness in application of the tweezers to the tick's body is not in the least disturbed by any incidental movement of the casing 36, as occasioned by either a single or a repeated depression of the plunger 34.

In the circuit of FIG. 5, the pulses produced could comprise peaks of opposite polarities, depending on the placement of a electrical ground at the secondary coil, as for example, at a tap (not shown) thereof.

In the case that the circuit of FIG. 5 is employed, the frequency of the pulses produced would depend on the size and mass of the movable one of the relay contacts 96. As presently contemplated, these pulses would typically be characterized by frequencies substantially in excess of 60 cycles, perhaps hundreds of cycles being a typical value.

From the above it can be seen that we have provided novel and improved tick removal apparati, and also a method which is considered safer than other, known methods, and which can be carried out in a minimum of time, with a good deal of precision. The method is characterized by improved safety against inadvertent infection of the host due to improper stimulus of the tick's body, or accidental rupture thereof.

The method and apparatus are thus seen to constitute a distinct advance and improvement in the field relating to treatment of tick "bites".

Variations and modifications are possible without departing from the spirit of the invention.

Each and every one of the appended claims defines an aspect of the invention which is separate and distinct from all others, and accordingly it is intended that each claim be treated in this manner when examined in the light of the prior art devices in any determination of novelty or validity.

What is claimed is:

1. A method of extracting a tick from the flesh of a victim, including the steps of applying a pair of jaws to the body of the tick and thereafter applying an electrical pulse to the body of the tick to jolt the tick into releasing its grip on the flesh of the victim.

2. The method of claim 1, wherein the electrical pulse comprises a waveform having consecutive peaks all of the same polarity.

3. The method of claim 1, wherein:
   a) the jaws are applied to the tick with one hand, and the electrical pulse is produced using another hand.

4. The method of claim 1, wherein:
   a) the pair of jaws constitutes a tweezers having prongs which are insulated from each other and the applying of an electrical pulse includes connecting the prongs respectively to flexible lead wires to which the pulse is initially applied.

5. The method of claim 1, wherein:
   a) the electrical pulse comprises a waveform having peaks of opposite polarities.

6. The method of claim 5, wherein:
   a) the electrical pulse comprises a waveform of a frequency substantially exceeding 60 cycles.

7. The method as set forth in claim 1, wherein:
   a) one of the jaws is electrically conductive, and the step of applying the electrical pulse to the body of the tick comprises electrically energizing the said conductive jaw while it is in physical contact with the body of the tick.

8. The method as set forth in claim 1, wherein:
   a) the electrical pulse is generated by a manually operable piezoelectric crystal generator.

9. The method as set forth in claim 8, wherein:
   a) additional pulses are generated at a rate controlled by the rate of manual operation of the piezoelectric crystal generator.

10. The method as set forth in claim 8, wherein:
    a) the piezoelectric crystal generator is capable of being manually operated in repeated, successive steps, while said jaws are in physical and electrical contact with the tick's body.

11. The method as set forth in claim 1, wherein the electrical pulse comprises a sparking voltage.

12. A method of two-handed extraction of a tick from the flesh of a victim, including the steps of applying a gripping instrument to the body of the tick with one hand, and actuating an electrical pulse generator with the other hand simultaneously applying an electrical pulse to said gripping instrument and the body of the tick held thereby so as to jolt the tick into loosening its grip on the flesh of the victim.

* * * * *